United States Patent
Aamodt et al.

(10) Patent No.: US 7,090,916 B2
(45) Date of Patent: *Aug. 15, 2006

(54) PAPER PRODUCT FOR USE IN STERILIZING AN AREA

(75) Inventors: James A. Aamodt, The Dalles, OR (US); John W. Colvin, Canby, OR (US)

(73) Assignee: CATHM, LLC, Canby, OR (US)

( * ) Notice: Subject to any disclaimer, the term of this patent is extended or adjusted under 35 U.S.C. 154(b) by 300 days.

This patent is subject to a terminal disclaimer.

(21) Appl. No.: 10/165,471

(22) Filed: Jun. 7, 2002

(65) Prior Publication Data

US 2003/0044314 A1    Mar. 6, 2003

Related U.S. Application Data

(63) Continuation-in-part of application No. 10/006,192, filed on Dec. 3, 2001, which is a continuation of application No. 09/302,937, filed on Apr. 30, 1999, now Pat. No. 6,325,969.

(51) Int. Cl.
    *A61L 2/00* (2006.01)
(52) U.S. Cl. .............. 428/308.8; 422/28; 422/29; 422/37; 428/311.11; 428/517
(58) Field of Classification Search .......... 422/28, 422/37, 29; 428/308.8, 311.11, 517
    See application file for complete search history.

(56) References Cited

U.S. PATENT DOCUMENTS

| | | | |
|---|---|---|---|
| 3,044,885 A | * | 7/1962 | Loehr .................. 424/413 |
| 4,404,306 A | * | 9/1983 | Daudt et al. ............. 524/262 |
| 4,430,381 A | | 2/1984 | Harvey et al. |
| 4,533,435 A | | 8/1985 | Intili |
| 4,738,847 A | | 4/1988 | Rothe et al. |
| 4,828,912 A | | 5/1989 | Hossain et al. |
| 4,897,304 A | | 1/1990 | Hossain et al. |
| 4,908,209 A | | 3/1990 | McIntosh, Jr. et al. |
| 5,227,242 A | | 7/1993 | Walter et al. |
| 6,022,627 A | | 2/2000 | Weder |
| 6,221,211 B1 | | 4/2001 | Hollenberg et al. |

FOREIGN PATENT DOCUMENTS

| | | |
|---|---|---|
| EP | 0 423 817 A | 4/1991 |
| EP | 0 768 032 A | 4/1997 |
| WO | WO 98 54279 A | 12/1998 |
| WO | WO 00 66185 A | 11/2000 |

* cited by examiner

Primary Examiner—Krisanne Jastrzab
(74) Attorney, Agent, or Firm—Holland & Bonzagni, P.C.; Mary R. Bonzagni, Esq.

(57) ABSTRACT

The present invention provides a paper product for use in sterilizing an area. The paper product contains at least one paper sheet or pellet containing one or more dry chemical materials, one or more dry deliquescent materials, or mixtures thereof. The dry chemical materials are either inactive antimicrobial or biocidal chemical materials or are capable of reacting with another chemical material to produce one or more active antimicrobial or biocidal chemical materials. When the paper product is placed in an atmosphere containing water vapor, the deliquescent material(s) attracts water and dissolves, thereby either hydrating and rendering active the inactive antimicrobial or biocidal chemical material(s), or providing a medium in which the chemical materials will react to produce one or more active antimicrobial or biocidal chemical materials.

11 Claims, 1 Drawing Sheet

PAPER PRODUCT FOR USE IN STERILIZING AN AREA

RELATED APPLICATIONS

This application is a continuation-in-part of U.S. patent application Ser. No. 10/006,192, filed Dec. 3, 2001, which is a continuation of U.S. patent application Ser. No. 09/302,937, filed Apr. 30, 1999, now U.S. Pat. No. 6,325,969.

FIELD OF THE INVENTION

The present invention relates to a paper product containing at least one chemical material to accomplish a variety of industrial and household tasks.

DESCRIPTION OF THE RELATED ART

Paper is typically formed from a mesh of fine fibers, generally of vegetable origin. Currently, wood pulp is the most common source for paper. However, other fibrous material such as cotton, flax, kenaf, hemp, or straw have been used in paper manufacture. Most commonly paper is produced in the form of thin sheets. However paper can also be manufactured in other physical forms such as compressed pellets.

Paper products currently enjoy widespread use in almost every field of human endeavor. Paper is used as sterile packaging for surgical instruments, and as a cheap, disposable covering for surfaces in treatment and operating rooms. In the food service industry, paper is universally utilized to store both solid and liquid foods, as well as to serve those foods to the consumer. Paper is also emerging as a major component in absorbent material for disposal of wastes from pets and other sources, for example in the material known as cat litter.

Given the wide uses for paper products, there is a need in the art for a paper product which receives, retains, and releases useful chemical species.

Unfortunately, paper provides a suitable environment for the growth of microorganisms. The ability of paper to support the growth of bacteria, molds, or fungi is attributable to the fact that paper is itself is derived from living tissue and contains residual organic material that can provide sustenance for microorganisms.

The unwanted growth of microorganisms poses a health hazard for many of the potential applications for paper products. For example, maintaining a sterile environment during the treatment of illness and injury has proven to dramatically reduce the possibility of infection. In the area of food services, maintaining a microorganism free environment prolongs the viability of foodstuffs, and enhances the effect of such processes as pasteurization. In waste disposal applications, reduction in the growth of microorganisms can cut down on noxious odors and the danger of infection to waste-handlers.

Therefore, there is also a need in the art for a paper product which can inhibit the growth of microorganisms, and which is cheap and easy to manufacture.

SUMMARY OF THE INVENTION

The present invention relates to a paper product that contains at least one chemical material. The impregnating chemical may beneficially react with other chemicals.

In one embodiment, paper is impregnated with hydrogen peroxide and acetic acid, and reaction between the hydrogen peroxide and acetic acid creates peracetic acid. Peracetic acid is both biocidal and volatile. The gaseous peracetic acid diffuses out of pores in the paper, creating a no-growth zone on the surface of and immediately surrounding the paper. In this manner, chemically impregnated paper in accordance with the present invention may promote a sterile environment useful for a wide variety of activities, for example in the treatment of illness/injury, or in the packaging/storage of foodstuffs.

In another embodiment, the chemical material(s) is used in conjunction with one or more deliquescent materials, and the materials either impregnated within, or contained on a surface of the paper product. In this embodiment, the chemical material(s) is either an antimicrobial or biocidal chemical material or is capable of reacting with another chemical material to produce an antimicrobial or biocidal chemical material.

In yet another embodiment, the chemical and deliquescent materials are added to the paper product during the paper-making process.

A method for sterilizing an area in accordance with the present invention comprises the steps of impregnating a paper product with a chemical material, placing the paper product in the area, and causing reaction of the impregnated chemical material to produce a biocidal compound.

A method for impregnating a paper product in accordance with one embodiment of the present invention comprises the steps of providing the paper product having pores and a surface, and exposing the surface of the paper product to at least one chemical which conveys biocidal properties to the paper product.

The present invention further relates to a papermaking process for preparing an antimicrobial or biocidal paper product, which comprises: (1) adding or applying one or more chemical and deliquescent materials to a dewatered fibrous web, where the chemical material(s) is either an antimicrobial or biocidal chemical material or is capable of reacting with another chemical material to produce an antimicrobial or biocidal chemical material; and (2) drying the web to a moisture level ranging from about 4 to about 6% by weight, based on the total weight of the web, thereby rendering inactive any antimicrobial or biocidal chemical material present in the dried web, wherein, when the paper product is placed in an atmosphere containing water vapor, the deliquescent material(s) attracts water and dissolves, thereby either hydrating and rendering active (i.e., activating) the inactive antimicrobial or biocidal chemical material(s), or allowing the chemical materials to react to produce one or more active antimicrobial or biocidal chemical materials.

A composition for producing peracetic acid in accordance with one embodiment of the present invention comprises a paper product impregnated with hydrogen peroxide and an acid.

In accordance with another embodiment of the present invention, a paper product for use in sterilizing an area is provided, which comprises: at least one paper sheet or pellet containing one or more dry chemical materials, one or more dry deliquescent materials, or mixtures thereof, wherein, the dry chemical material(s) is either an inactive antimicrobial or biocidal chemical material or is capable of reacting with another chemical material to produce one or more active antimicrobial or biocidal chemical materials, and wherein, when the paper product is placed in an atmosphere containing water vapor, the deliquescent material(s) attracts water and dissolves, thereby activating the inactive antimicrobial or biocidal chemical material(s), or providing a medium in which the chemical materials will react to produce one or more active antimicrobial or biocidal chemical materials.

The term "sterilizing," as used herein, means to render or make free from microorganisms, but not live bacteria or bacterial spores. It is noted, however, that some of the embodiments contemplated by way of the present invention may also serve to render an area free from live bacteria or bacterial spores.

In a preferred embodiment, the activatable, antimicrobial or biocidal paper product described immediately hereinabove is prepared by a papermaking process which comprises: (1) adding or applying one or more chemical materials and one or more deliquescent materials to a dewatered fibrous web; and (2) drying the web to a moisture level ranging from about 4 to about 6% by weight, based on the total weight of the web.

The features and advantages of the present invention will be understood upon consideration of the following detailed description of the invention and the accompanying drawings.

DETAILED DESCRIPTION

Figure 1:
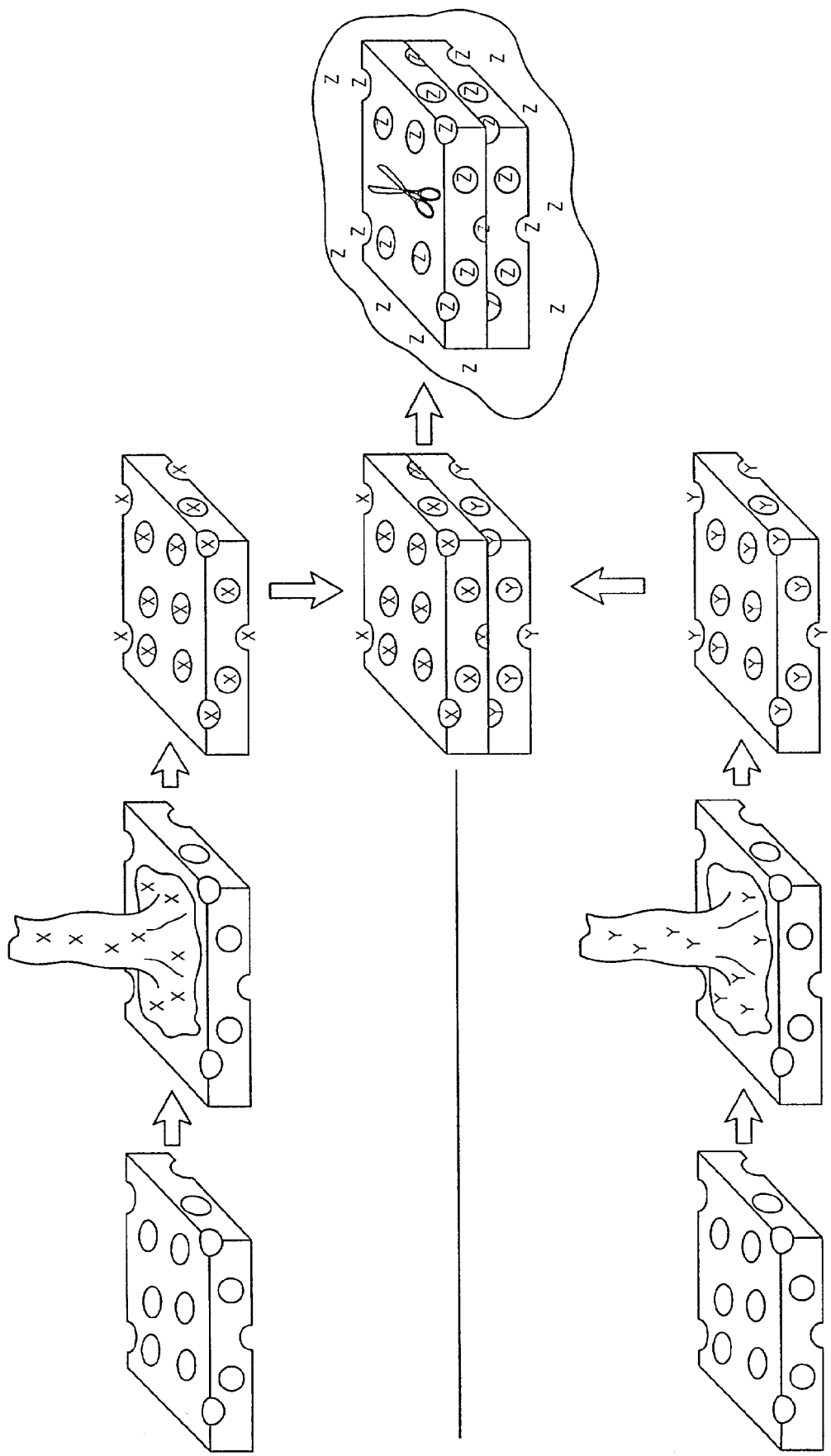
FIG. 1 illustrates a method for creating a sterile field utilizing chemically impregnated sheets of paper in accordance with one embodiment of the present invention.

The present invention relates to a paper product that has been impregnated with at least one chemical material. Reaction and/or diffusion of this chemical out of the pores of the paper gives rise to a number of beneficial properties. In particular, diffusion of an impregnating volatile antimicrobial or biocidal agent creates a sterile environment at the surface and in the immediate vicinity of the paper.

The present invention further relates to a paper product containing dry chemical and deliquescent materials. As noted above, the dry chemical material(s) is either a dehydrated and thus inactive antimicrobial or biocidal material, or is capable of reacting with another chemical material to produce an active antimicrobial or biocidal chemical material. As also noted above, when the paper product is placed in an environment containing water vapor, the deliquescent material(s) attracts water and dissolves, thereby either activating (via hydration) the inactive antimicrobial or biocidal chemical material(s), or providing a medium in which the chemical materials will react to produce one or more active antimicrobial or biocidal chemical materials.

Paper is a highly porous material. These pores are defined by space between the extremely fine vegetable fibers making up the mesh. The pores in the paper can receive and contain a wide variety of chemical materials.

For example, the pores in paper can be impregnated with precursors of chlorine dioxide ($ClO_2$), a gas useful for killing biological contaminants (such as microorganisms, mold, fungi, yeast and bacteria). The biocidal nature of $ClO_2$ is attributable to its high oxidation potential.

Chlorine dioxide can be produced in many ways. For example, it is known to generate chlorine dioxide by adding an acid to a metal chlorite solution. Chlorine dioxide can also be generated by adding water to a powdered composition such as ferric sulfate or ferric chloride (or other dry composition). An activated dry composition which absorbs water from the air and releases chlorine dioxide over time may also be prepared.

In a first class of embodiments of the present invention, a sheet of paper is successively impregnated with sodium chlorite and acetic acid, or one sheet of paper impregnated with sodium chlorite is placed into contact with another sheet of paper impregnated with acetic acid. Mixing by co-diffusion of the two chemicals causes in the following reaction:

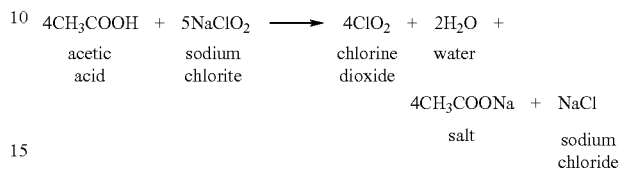

The volatile chlorine dioxide then diffuses from pores of the paper into the surrounding environment. The chlorine dioxide suppresses growth of bacteria, molds, or fungi on the surface of the paper or in areas immediately surrounding the paper.

Acetic acid is only one acid that can generate chlorine dioxide in accordance with the present invention. Sulfuric acid, phosphoric acid, and propionic acid can also react with sodium chlorite to produce chlorine dioxide. Moreover, these acids can also react with paper impregnated with sodium chlorate to produce chlorine dioxide.

FIG. 1 illustrates one embodiment of the present invention, wherein separate sheets of paper 10A and 10B are impregnated with sodium chlorite X and acetic acid Y, respectively. Impregnated papers 10A and 10B are separately stored and transported to the site of use, such as a hospital operating room. At the point of use, impregnated papers 10A and 10B are placed in physical contact. Co-diffusion of the sodium chlorite X and acetic acid Y promotes reaction between these chemicals, forming volatile chlorine dioxide Z. Chlorine dioxide Z outgasses from combined papers 10C, inhibiting the growth of microorganisms on the surface of the combined papers 10C as well as in immediate vicinity 10D of combined papers 10C. This outgassing provides a sterile environment for surgical instrument 12.

In another embodiment of the present invention, a paper product in the form of pellets is impregnated with sodium chlorite and acetic acid. Alternatively, a first bed of paper pellets is impregnated with sodium chlorite, and a second bed of paper pellets is impregnated with acetic acid. Mixing together of pellets from the two beds can promote the formation of chlorine dioxide.

In a further alternative embodiment of the present invention, a paper product in the form of sheets or pellets is successively impregnated with hydrogen peroxide and an acid. Mixing by co-diffusion of the two impregnating compounds produces a peracid. Acids which may be mixed with hydrogen peroxide to produce the corresponding peracid include but are not limited to: acetic acid; propionic acid; citric acid; benezoic acid; phosphoric acid; lactic acid; butyric acid; pentenoic acid; succinic acid; glutaric acid; sorbic acid; and glycolic acid.

The following chemical reaction shows the specific reaction between acetic acid and hydrogen peroxide to produce peracetic acid:

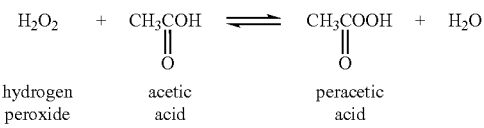

hydrogen peroxide    acetic acid    peracetic acid

Like chlorine dioxide, peracetic acid has a high oxidation potential and corresponding biocidal properties. Diffusing peracetic acid creates the same type of sterile field discussed above in connection with chlorine dioxide.

In yet a further embodiment of the present invention, the paper product contains chemical and deliquescent materials. For example, the paper product may comprise a paper sheet or pellet containing both the chemical and deliquescent materials. In the alternative, the paper product may comprise at least two paper sheets or pellets, where each sheet or pellet contains either the chemical material(s), or the deliquescent material(s). The chemical and deliquescent materials may also be contained between two paper sheets. For example, a mixture of these materials may be contained in one or more sealed pockets that are formed by the two paper sheets.

The deliquescent material(s) residing in the paper product of the present invention will attract water and dissolve when the paper product is placed in a moist environment (i.e., ambient humidity levels of greater than or equal to 15%), thereby either activating (via hydration) the antimicrobial or biocidal chemical material(s), or providing a medium in which the chemical materials will react to produce one or more active antimicrobial or biocidal chemical materials.

Preferably, the deliquescent material is selected from the group including alumina, calcium chloride, lithium chloride, magnesium chloride, magnesium nitrate, silica gel and mixtures thereof, with a more preferred deliquescent material being calcium chloride.

The weight ratio of the chemical material(s) to the deliquescent material(s) ranges from about 1:1 to about 10:1 (preferably from about 1:1 to about 3:1), with the total amount of these materials present in the inventive paper product ranging from about 5 to about 20% by weight (preferably from about 5 to about 15% by weight), based on the total weight of the paper product.

The chemical and deliquescent materials may be added to the paper product of the present invention during the papermaking process or during a subsequent converting process.

While it is desirable in terms of process economics to add the chemical material(s) during manufacture of the inventive paper product, the chemical material(s) is either rendered inactive, or incapable of reacting with another chemical material, as a result of the significant water loss that occurs during the papermaking process. The presence of the deliquescent material(s) serves to solve this problem by attracting moisture and dissolving.

As is well known to those skilled in the art, the widely accepted Fourdrinier papermaking process involves depositing a furnish (i.e., a fibrous slurry containing e.g., 0.5% by weight stock (i.e., virgin, recycled or mixed virgin and recycled pulp of wood fibers, fillers, sizing and/or dyes) and 99.5% by weight water) from a headbox onto a fast-moving foraminous conveyor belt or screen, which provides a surface upon which the paper is formed. As the furnish moves along, gravity and suction boxes located under the conveyor belt or screen draw the water from the furnish forming a fibrous web.

Upon leaving the so-called "wet-end" of the papermaking machine, the fibrous web still contains a considerable amount of water. The web is therefore directed toward a press section, which can be a series of heavy rotating cylinders, which serve to press the water from the web, further compacting it and reducing its water content, typically to about 70% by weight.

Following pressing, the paper web is dried in the main dryer section of the papermaking machine. In the drying section, which is typically the longest section of the papermaking machine, hot air or steam-heated cylinders contact both sides of the web, substantially drying the web by evaporating the water to a level of approximately 5% by weight of the paper. It is noted that the maximum temperature in the main dryer section may exceed 71° C.

The dried web is then optionally surface sized at a size press (e.g., of the puddle or metering type) where the amount of pickup can be controlled. Sizing operations are carried out primarily to provide paper with surface strength and control of penetration by aqueous solutions. The treatment also improves the surface characteristics and certain physical properties of the paper. During surface sizing, surface voids in the sheet are filled with starch or other binder particles. It is noted that the size press can be used to add a variety of agents for a variety of purposes (e.g., starch and polyvinyl alcohol for strength, pigments such as calcium carbonate, clay for improving the brightness and smoothness of the product).

The size press-treated paper is then dried in a secondary dryer section of the papermaking machine to a moisture level of from about 4 to about 6%. Maximum temperatures in the secondary dryer section may also exceed 71° C.

As explained in more detail below, the chemical and deliquescent materials are preferably added at the size press of the papermaking machine.

In one embodiment of the present invention, the chemical material(s) is a solid and the mixture of the chemical and deliquescent materials is a physical mixture. In a preferred embodiment, the mixture is an intimate, physical mixture. For example, the chemical and deliquescent materials may be in the form of agglomerates prepared by e.g. grinding the materials, mixing them to substantial homogeneity, spraying the mixture with an agglomerating fluid, and forming agglomerates on a pan agglomerator followed by drying. In the alternative, an aqueous solution of the deliquescent material(s) may be sprayed onto the chemical material(s) and then dried.

In a more preferred embodiment, the intimate, physical mixture is in the form of granules prepared from a compacted blend of the chemical and deliquescent materials. More specifically, the chemical and deliquescent material are mixed, compacted and granulated.

In another embodiment, the chemical material(s) is a liquid and the mixture of the chemical and deliquescent materials takes the form of a solution, emulsion or the like.

The physical or solid mixtures of the chemical and deliquescent materials described above may be applied to the dewatered fibrous web at the size press using conventional application techniques. In one embodiment, a supersaturated aqueous solution of the physical or solid mixture is prepared and impregnated into the web by any method suitable for the application of liquid impregnates, including dipping, flood coating, spray coating or metered dosing. More specialized techniques, such as Meyer Rod, floating knife or doctor blade, which are typically used to impregnate liquids into absorbent sheets, may also be used.

The liquid mixtures (i.e., solutions, emulsions, or the like) of the chemical and deliquescent materials described above may be applied to the dewatered fibrous web at the size press by conventional methods, including those methods noted above.

When the solid or liquid mixture is to be contained on a surface of the paper sheet, covering either the entire surface or only select areas or pockets, the solid or liquid mixture is applied to the surface of the paper sheet, a second paper sheet is then applied and the sheets sealed together using a laminating adhesive so as to trap the mixture between the paper sheets. In a preferred embodiment, the paper sheets are sealed together in a pattern so that a pattern of pockets or cells are formed containing the solid or liquid mixture.

In yet another further embodiment of the present invention, the chemical and deliquescent materials are used in conjunction with one or more types of carrier materials.

In one such further embodiment, the carrier material is a porous carrier material that serves to immobilize the chemical and deliquescent materials by adsorption, absorption or covalent bonding. By way of their porous structure, the carrier materials allow for increases in the chemical and deliquescent material loadings within the inventive paper product. Moreover, once the antimicrobial or biocidal chemical material(s) has been activated or produced, the porous carrier material will serve to check or delay the release of these materials from the paper product, increasing the product's useful life.

Suitable porous carrier materials include, but are not limited to, siliceous minerals such as natural or synthetic clays (bentonite, attapulgite, fuller's earth, sepiolite, kaolin), kenaf fibers, zeolite molecular sieves, synthetic porous silicas and silicates.

The carrier material, which is not readily lost during dewatering, may be added at any stage during the papermaking process.

For example, the carrier material may be added to the pulp used to prepare the inventive paper product at the headbox. In this embodiment, the chemical and deliquescent materials would be adsorbed, absorbed or bonded to the carrier material when the chemical and deliquescent materials are applied to the dewatered fibrous web at the size press.

The carrier material(s) may also be added at the size press of the papermaking machine. In this embodiment, the chemical and deliquescent materials are applied to the carrier material prior to adding the carrier material to the web by use of conventional techniques such as spraying, wet mixing, dipping, or the like.

In yet another further embodiment of the present invention, the chemical and deliquescent materials are used in conjunction with one or more superabsorbent materials, and preferably are used in conjunction with one or more carrier and superabsorbent materials.

The term "superabsorbent" or "superabsorbent material" means a water-swellable, water-insoluble organic or inorganic material capable of absorbing at least about 20 times its weight and, more preferably, at least about 30 times its weight in an aqueous solution. The superabsorbent materials can be natural, synthetic, modified natural polymers and materials, inorganic materials (i.e., silica gels) or organic compounds (i.e., cross-linked polymers).

Suitable superabsorbent materials include, but are not limited to: (1) synthetic superabsorbent material polymers such as alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone, poly(vinyl-morpholinone), poly(vinyl alcohol), and mixtures and copolymers thereof, (2) natural and modified natural polymers such as hydrolyzed acrylonitrile-grafted starch, acrylic acid grafted starch, methyl cellulose, chitosan, carboxymethyl cellulose, hydroxypropyl cellulose and natural gums (e.g., alginates, xanthan gum, locust bean gum); and (3) mixtures of natural and wholly or partially synthetic superabsorbent polymers.

The superabsorbent materials may be considered secondary carriers that serve to absorb the antimicrobial or biocidal chemical material(s) upon activation or formation, thereafter allowing for the controlled release of these materials from the paper product, increasing or further increasing the product's useful life.

The superabsorbent material, like the carrier material, is not readily lost during de-watering, and may be added at any stage during the papermaking process.

A variety of methods may be utilized to impregnate the paper with chemical materials during e.g. a subsequent converting process. For example, the paper may be dunked or immersed in a bath containing the chemical, with the liquid chemical drawn into the pores of the paper through the process of diffusion. Alternatively, the chemical may be sprayed upon the surface of the paper, with impregnation of the paper accomplished through diffusion of the chemical from the paper's surface into the underlying pores.

The present invention is applicable to impregnate a variety of paper products. Paper made from softwood pulp, kenaf, flax, and hemp are all suitable for chemical impregnation in accordance with the present invention.

In order to further illustrate the present invention, the following experimental examples are described. Each of these examples illustrates impregnation of paper with chemicals that impart biocidal properties.

EXAMPLE NUMBER 1

The antimicrobial properties of a number of samples of impregnated kenaf papers was determined by exposing *E. coli* bacteria during its growth period to the impregnated paper. This was done by using a zone of inhibition test.

A half inch square of the impregnated sample kenaf paper was placed in the center of a Petri dish containing an agar and *E. coli* bacteria spread on the agar surface. Where *E. coli* bacteria were unable to multiply to form visible colonies due to the effects of the test paper, the agar media remained clear. This clear area is known as the zone of inhibition. Bacteria outside of this zone of inhibition are not affected by their proximity to the sample and grow to form visible colonies.

A number of samples were prepared according to TABLE 1:

TABLE 1

| Sample Number | Sample Components (all % by weight) |
|---|---|
| 1 | 35% aqueous hydrogen peroxide |
|   | 99% acetic acid |
| 2 | paper only-no impregnated chemicals |
| 3 | 5% d-limonene in water |
| 4 | 5% d-limonene in water |
|   | 35% aqueous hydrogen peroxide |
| 5 | 50% aqueous potassium sorbate |
|   | 99% acetic acid |
| 6 | 50% aqueous potassium sorbate |
|   | 5% d-limonene in water |
| 7 | 50% aqueous potassium sorbate |
|   | 35% aqueous hydrogen peroxide |

The chemicals to be impregnated in each sample were sprayed onto sheets of kenaf paper in equal parts of 2 cc/ft$^2$ of paper surface area. The paper was allowed to dry, and a ½"×½" square of the impregnated paper was cut to serve as a sample.

A petri dish with Standard Plate Count Agar was inoculated with *E. coli* bacteria by using a bottle with 99 ml sterile phosphate-buffered dilution water, to which is added one loopful of diluted *E. coli* culture. A sterile cotton swab was dipped into the dilution water-containing the *E. coli* culture, then the swab was liberally wiped over the entire surface of the agar. After this, the ½ inch square of the paper sample was placed in the middle of the dish, and the dish was then sealed. After two days growth at 35° C., the zone of inhibition around the paper was measured from all four sides and averaged.

The results of the zone of inhibition test for *E. coli* bacteria for the samples listed in TABLE 1 are shown in TABLE 2:

TABLE 2

Zone of Inhibition Test Using *E. Coli* Bacteria

| Sample # | Side #1 | Side #2 | Side #3 | Side #4 | Avg. Length |
|---|---|---|---|---|---|
| 1 | 2.6 cm | 2.7 cm | 2.6 cm | 2.6 cm | 2.63 cm |
| 2 | 0.0 cm | 0.0 cm | 0.0 cm | 0.0 cm | 0.0 cm |
| 3 | 0.0 cm | 0.0 cm | 0.0 cm | 0.0 cm | 0.0 cm |
| 4 | 2.9 cm | 2.8 cm | 3.0 cm | 2.7 cm | 2.85 cm |
| 5 | 1.3 cm | 1.0 cm | 1.0 cm | 1.1 cm | 1.1 cm |
| 6 | 1.0 cm | 1.1 cm | 1.0 cm | 1.0 cm | 1.03 cm |
| 7 | 0.5 cm | 0.6 cm | 0.5 cm | 0.5 cm | 0.53 cm |

Review of TABLE 2 indicates that sample no. 4 (5% d-limonene/35% aqueous hydrogen peroxide) was most effective in inhibiting the growth of the *E. Coli* bacteria. Sample no. 1 (99% acetic acid/35% aqueous hydrogen peroxide) was the next most effective mixture. Neither the control (sample no. 2) nor d-limonene alone (sample no. 3) showed anyeffectiveness against the *E. Coli* bacteria.

EXAMPLE NUMBER 2

A second zone of inhibition test was next performed to test the ability of the samples of TABLE 1 to inhibit growth of the Penicillium mold.

A Petri dish with Standard Plate Count Agar was inoculated with a wild strain of the Penicillium mold by using a bottle with 99 ml sterile phosphate-buffered dilution water, to which was added a moistened cotton swab that has been rubbed on the top of a growing colony of Penicillium. A new sterile cotton swab was dipped into the dilution water containing the Penicillium culture, then the swab was liberally wiped over the entire surface of the agar. After this, a ½ inch square of the paper sample was placed in the middle of the dish, and the dish was then sealed.

After four days growth at room temperature, the zone of inhibition was measured from all four sides and averaged. The results are shown in TABLE 3:

TABLE 3

Zone of Inhibition Test Using Wild Strain of Penicillium Mold

| Sample # | Side #1 | Side #2 | Side #3 | Side #4 | Avg. Length |
|---|---|---|---|---|---|
| 1 | 1.8 cm | 1.7 cm | 1.8 cm | 1.9 cm | 1.8 cm |
| 2 | 0.0 cm | 0.0 cm | 0.0 cm | 0.0 cm | 0.0 cm |
| 3 | 0.0 cm | 0.0 cm | 0.0 cm | 0.0 cm | 0.0 cm |
| 4 | 2.3 cm | 2.2 cm | 2.3 cm | 2.2 cm | 2.25 cm |
| 5 | 1.1 cm | 1.0 cm | 1.0 cm | 1.0 cm | 1.02 cm |
| 6 | 0.0 cm | 0.0 cm | 0.0 cm | 0.0 cm | 0.0 cm |
| 7 | 0.0 cm | 0.0 cm | 0.0 cm | 0.0 cm | 0.0 cm |

Review of TABLE 3 indicates that sample no. 4 (5% d-limonene/35% aqueous hydrogen peroxide) was again most effective at inhibiting the growth of microorganisms. Sample no. 1 (99% acetic acid/35% aqueous hydrogen peroxide) was again the next most effective mixture. Neither the control (sample no. 2) nor d-limonene alone (sample no. 3) showed anyeffectiveness against the Penicillium mold.

EXAMPLE NUMBER 3

To evaluate the effect upon biocidal activity of the type of paper impregnated with chemical species, a third zone of inhibition test was conducted. This test utilized a second set of samples prepared according to TABLE 4:

TABLE 4

| Sample Number | Paper Type | Sample Components (all % by weight) |
|---|---|---|
| 8 | flax | 50% aqueous citric acid 35% aqueous hydrogen peroxide |
| 9 | hemp | 50% aqueous citric acid 35% aqueous hydrogen peroxide |
| 10 | kenaf | 50% aqueous citric acid 35% aqueous hydrogen peroxide |
| 11 | wood pulp | 5% d-limonene in water 35% aqueous hydrogen peroxide |
| 12 | kenaf | 100% 50% aqueous citric acid |
| 13 | kenaf | 100% 35% aqueous hydrogen peroxide |

Again, the components of each sample were sprayed onto the paper in equal parts of 2 cc/ft$^2$ of paper surface area. The paper was allowed to dry, and a ½"×½" square of the impregnated paper were then cut to serve as a sample.

A zone of inhibition test was then performed in the presence of *E. coli* bacteria, as otherwise described above in Example Number 1. The results are shown in TABLE 5:

TABLE 5

Zone of Inhibition Test Using *E. Coli* Bacteria

| Sample # | Side #1 | Side #2 | Side #3 | Side #4 | Avg. Length |
|---|---|---|---|---|---|
| 8 | 1.6 cm | 1.4 cm | 2.0 cm | 2.4 cm | 1.85 cm |
| 9 | 1.1 cm | 1.6 cm | 1.8 cm | 1.3 cm | 1.45 cm |
| 10 | 1.9 cm | 2.4 cm | 2.6 cm | 2.7 cm | 2.40 cm |
| 11 | >3.3 cm | 3.0 cm | 2.8 cm | 2.9 cm | >3.00 cm |
| 12 | 1.6 cm | 1.5 cm | 1.4 cm | 1.5 cm | 1.50 cm |
| 13 | 2.4 cm | 2.9 cm | 2.8 cm | 2.8 cm | 2.73 cm |

Review of TABLE 5 indicates that sample no. 11 (50% citric acid/35% aqueous hydrogen peroxide in wood pulp paper) was the most effective at inhibiting the growth of the *E. Coli* bacteria. Sample no. 13 (35% aqueous hydrogen peroxide in kenaf paper) was the next most effective mixture. Hemp paper impregnated with the citric acid/hydrogenperoxide combination evidenced the least biocide activity.

EXAMPLE NUMBER 4

A zone of inhibition test of the samples of TABLE 4 in the presence of the Penicillium mold. The experiment was otherwise conducted in the general manner described above in connection with Example Number 2. The results are shown below in TABLE 6:

TABLE 6

Zone of Inhibition Test Using Wild Strain of Penicillium Mold

| Sample # | Side #1 | Side #2 | Side #3 | Side #4 | Avg. Length |
|---|---|---|---|---|---|
| 8 | 1.9 cm | 2.0 cm | 2.0 cm | 1.8 cm | 1.92 cm |
| 9 | 2.3 cm | 2.0 cm | 2.1 cm | 1.9 cm | 2.07 cm |
| 10 | 2.9 cm | 2.7 cm | 2.8 cm | 2.9 cm | 2.82 cm |
| 11 | 2.6 cm | 2.3 cm | 2.2 cm | 2.4 cm | 2.37 cm |
| 12 | 0.0 cm | 0.0 cm | 0.0 cm | 0.0 cm | 0.0 cm |
| 13 | 1.9 cm | 2.0 cm | 2.1 cm | 1.9 cm | 1.97 cm |

Review of TABLE 6 indicates that sample no. 9 (50% citric acid/35% aqueous hydrogen peroxide in kenaf paper) was the most effective at inhibiting the growth of the Penicillium mold. Sample no. 11 (50% citric acid/35% aqueous hydrogen peroxide in wood paper) was the next most effective combination. Kenaf paper impregnated with citric acid exhibited no biocidal activity.

The impregnated paper product in accordance with the present invention offers a number of important advantages. One advantage is that the paper can be impregnated with the chemical species directly during the papermaking process.

Yet another advantage of chemically-impregnated paper in accordance with the present invention is that its relatively cheap cost facilitates replacement when the impregnating chemical material becomes spent or exhausted. This is particularly important in medical treatment applications having a low tolerance for contamination, which require frequent replacement of materials in order to maintain the integrity of the sterile field.

Another important advantage of the present invention is its environmental compatibility. Examples 1–4 reveal that impregnated kenaf paper has significant biocidal capability. Kenaf is an annual plant having a paper producing potential approximating that of wood, making it an environmentally-friendly alternative paper source. Moreover, the impregnating chemicals acetic acid, citric acid, and d-limonene are both readily obtained from natural sources. Acetic acid can be obtained by fermentation, citric acid is present in fruits, and d-limonene is derived from orange peels.

Although the invention has been described in connection with specific embodiments, it must be understood that the invention as claimed should not be unduly limited to these embodiments. Various other modifications and alterations in the structure and process will be apparent to those skilled in the art without departing from the scope of the present invention.

For example, while the embodiment of the present invention shown in FIG. 1 describes generating chlorine dioxide from the combination of sodium chlorite and acetic acid, the invention is not limited to these impregnated chemicals. The combination of sodium chlorate and sulfuric acid would also function to generate chlorine dioxide. This is also true for the combination of either sodium chlorate or sodium chlorite and either ferric chlorate or ferric sulfate.

Moreover, while experimental results have been reported above in conjunction with impregnation of paper with chemicals imparting biocidal activity, paper could be impregnated with a wide variety of other types of chemicals in accordance with the present invention. TABLE 7 provides a partial listing of possible chemicals and chemical combinations suitable for impregnating paper in accordance with the present invention:

TABLE 7

| IMPREGNATING CHEMICAL SPECIES | PRODUCT CHEMICAL SPECIES | USES FOR PRODUCT CHEMICAL SPECIES |
|---|---|---|
| 1) hydrogen peroxide 2) acid (ex. acetic acid) | Peracid | biocide |
| 1) sodium chlorite/ sodium chlorate 2) acid (ex. acetic acid)/or metal salt (ex. ferric sulfate) | Chlorine dioxide | biocide |
| phosphoric acid | $(NH_4)_2HPO_4$ | odor control (absorption of ammonia) |
| 1) permanganate (ex. potassium permanganate) 2) quarternary ammonium cation (ex. cetyltrimethyl-ammonium) | $CO_2 + H_2O$ | oxidation and removal of organic contaminants from a mixture |
| potassium hydroxide | $KClO_2 + KCLO_4$ | removal of $ClO_2$ |
| sodium sulfite/ or sodium bisulfite | $S_2O_5 = H^+{}_3ClO_3$ | removal of $ClO_2$ |
| manganese dioxide | — | molecular sieve (filtration) |

Examples of the chemicals (or inhibitors of chemicals) usefully impregnated into paper products (e.g. sheets of paper or paper pellets) include the following: acids such as acetic acid, amino acids, benezoic acid, butyric acid, calcium disodium EDTA, citric acid, glutaric acid, glycolic acid, lactic acid, malic acid, pentenoic acid, peracetic acid, percitric acid, phosphoric acid, propionic acid, succinic acid, sulfuric acid and tartaric acid; oils/extracts such as castor oil, catnip oil, cedar oil, cinnamon leaf oil, citronella oil, cloves oil, corn oil, cottonseed oil, eugenol, garlic oil, geraniol, geranium oil/extract, grapefruit seed extract, grape seed oil/extract, lemongrass oil, d-limonene, linseed oil, orange peel oil/extract, oregano oil/extract, peppermint oil/extract, rosemary oil/extract, sesame oil, soybean oil, Texas cedarwood oil/extract and thyme oil/extract; salts such as calcium chloride, cobalt chloride, cobalt sulfate, copper chloride, copper sulfate, ferric chloride, ferric sulfate, lauryl sulfate, magnesium chloride, magnesium sulfate, manganese chloride, manganese sulfate, 2-phenethyl propionate, potassium chloride, potassium sorbate, sodium acid pyrophosphate, sodium benzoate, sodium bisulfite, sodium chlorate, sodium chlorite, sodium lauryl sulfate, sodium metabisulfite, sodium sulfite, zinc chloride and zinc sulfate; and vitamins such as vitamin B complex (e.g., folic acid), vitamin C or ascorbic acid, vitamin E (e.g., α-tocopherol) and vitamin K or derivatives of 2-methyl-1,4-naphthoquinone. Also included as useful chemicals are chlorine, chloroamines, corn gluten meal, cranberry concentrate, free amines, hydrogen peroxide, iron, manganese dioxide, permanganates (including but not limited to potassium permanganate), potassium hydroxide, quarternary ammonium cation (including but not limited to cetyltrimethylammonium chloride), sodium selenate, sulfur dioxide, urea, white pepper and zinc.

As will be readily appreciated by those skilled in the art, some of the above-referenced chemicals (e.g., catnip oil, citronella oil, cloves oil, rosemary oil/extract, thyme oil/extract, etc.) may further demonstrate insecticidal or pesticidal properties.

Given the multitude of embodiments described above, it is therefore intended that the following claims define the scope of the present invention, and that the compositions and methods within the scope of these claims and their equivalents be covered hereby.

The invention claimed is:

1. A paper product for use in sterilizing an area, which comprises: at least one paper sheet or pellet; and one or more dry chemical materials and one or more dry deliquescent materials, contained on and/or within the at least one paper sheet or pellet,
   wherein said one or more dry chemical materials are either inactive antimicrobial or biocidal chemical materials or are capable of reacting with another chemical material to produce one or more active antimicrobial or biocidal chemical materials, and are selected from the group of citric acid, cinnamon leaf oil, citronella oil, lemongrass oil, sodium acid pyrophosphate, ascorbic acid and mixtures thereof,
   wherein said one or more dry deliquescent materials are selected from the group of alumina, calcium chloride, lithium chloride, magnesium chloride, magnesium nitrate, silica gel and mixtures thereof, and
   wherein, when said paper product is placed in an atmosphere containing water vapor, said one or more deliquescent materials attract water and dissolve, thereby either hydrating and rendering active said inactive antimicrobial or biocidal chemical materials, or providing a medium in which said chemical materials will react to produce one or more active antimicrobial or biocidal chemical materials.

2. The paper product of claim 1, which comprises a paper sheet or pellet impregnated with a mixture of said dry chemical and deliquescent materials.

3. The paper product of claim 1, which comprises contiguous first and second paper sheets, wherein said first paper sheet is impregnated with said one or more dry chemical materials, and wherein said second paper sheet is impregnated with said one or more dry deliquescent materials.

4. The paper product of claim 1, which comprises contiguous first and second paper pellets, wherein said first paper pellet is impregnated with said one or more dry chemical materials, and wherein said second paper pellet is impregnated with said one or more dry deliquescent materials.

5. The paper product of claim 1, which comprises contiguous first and second paper sheets, wherein a mixture of said dry chemical and deliquescent materials is contained between said first and said second paper sheets.

6. The paper product of claim 5, wherein said mixture is contained in pockets formed by said first and second paper sheets.

7. The paper product of claim 1, wherein said paper sheet or pellet is formed from at least one of softwood pulp, kenaf, flax and hemp.

8. The paper product of claim 1, wherein said one or more dry chemical materials are contained on a granular carrier material, wherein said granular carrier material is selected from the group of siliceous minerals, kenaf fibers, zeolite molecular sieves, synthetic porous silicas, silicates and mixtures thereof.

9. The paper product of claim 1, wherein said one or more dry deliquescent materials are contained on a granular carrier material, wherein said granular carrier material is selected from the group of siliceous minerals, kenaf fibers, zeolite molecular sieves, synthetic porous silicas, silicates and mixtures thereof.

10. The paper product of claim 1, wherein said at least one paper sheet or pellet further contains one or more dry superabsorbent materials.

11. A paper product for use in sterilizing an area, which consists essentially of: at least one paper sheet or pellet; and one or more dry chemical materials and one or more dry deliquescent materials, contained on and/or within the at least one paper sheet or pellet,
    wherein said one or more dry chemical materials are either inactive antimicrobial or biocidal chemical materials or are capable of reacting with another chemical material to produce one or more active antimicrobial or biocidal chemical materials, and are selected from the group of citric acid, cinnamon leaf oil, citronella oil, lemongrass oil, sodium acid pyrophosphate, ascorbic acid and mixtures thereof,
    wherein said one or more dry deliquescent materials are selected from the group of alumina, calcium chloride, lithium chloride, magnesium chloride, magnesium nitrate, silica gel and mixtures thereof, and
    wherein, when said paper product is placed in an atmosphere containing water vapor, said one or more deliquescent materials attract water and dissolve, thereby either hydrating and rendering active said inactive antimicrobial or biocidal chemical materials, or providing a medium in which said chemical materials will react to produce one or more active antimicrobial or biocidal chemical materials.

* * * * *